United States Patent [19]

Sincock

[11] Patent Number: 5,047,019

[45] Date of Patent: Sep. 10, 1991

[54] DEVICE FOR THE SAFE REMOVAL AND DISPOSAL OF SHARPS FROM MEDICAL TOOLS

[75] Inventor: Brian F. Sincock, Dernancourt, Australia

[73] Assignee: Ausmedics Pty. Ltd., Port Lincoln, Australia

[21] Appl. No.: 528,963

[22] Filed: May 22, 1990

Related U.S. Application Data

[63] Continuation-in-part of Ser. No. 265,707, Nov. 1, 1988, Pat. No. 4,973,315, and a continuation-in-part of Ser. No. 497,638, Mar. 23, 1990.

[30] Foreign Application Priority Data

Nov. 11, 1987 [AU] Australia .................................. PI5348
Oct. 26, 1989 [AU] Australia .................................. PH7069

[51] Int. Cl.⁵ .............................................. A61M 5/32
[52] U.S. Cl. .................................... 604/192; 206/366; 206/486

[58] Field of Search ....................... 604/192, 263, 187; 206/363-370, 438, 486

[56] References Cited

U.S. PATENT DOCUMENTS

D. 271,239 11/1983 Lemieux et al. ................. 604/192 X
4,798,292 1/1989 Hauze .............................. 604/192 X Primary Examiner—John D. Yasko
Attorney, Agent, or Firm—Fish & Richardson

[57] ABSTRACT

An apparatus provides for the safe removal and disposal of medical sharps. In a preferred embodiment, the apparatus comprises a tray with a plurality of apertures in a planar surface, with each aperture receiving and supporting a sheath for the disposal of medical sharps. The apparatus includes a cover for the tray which comprises a plurality of apertures, such that the apertures in the cover are arranged to substantially correspond to an arrangement of apertures in the tray.

21 Claims, 7 Drawing Sheets

DEVICE FOR THE SAFE REMOVAL AND DISPOSAL OF SHARPS FROM MEDICAL TOOLS

This application is a continuation-in-part of U.S. Ser. No. 07/265,707, filed Nov. 1, 1988, now U.S. Pat. No. 4,973,315, U.S. Ser. No. 07/497,638, filed Mar. 23, 1990.

This invention relates to improvements in the removal of sharp pointed sections of medical instruments and their safe disposal or the disposal of sharp pointed medical instruments or sharps as they are known.

Sharps may include needles for hypodermic syringes, canulas, scalpels, catheters or any other sharp pointed instruments used in medical treatment and which are generally of the disposable kind but which, because they have been used for treating ill people, may be carrying disease organisms or other infectious bodies.

To meet stringent health and safety regulations and to minimize transmission of bacteria, viruses, disease or other organisms having the potential to create disease or illness it is now a practice to dispose of the sharp or needle section of a medical device or the complete tool with the sharp or needle section attached once the medical tool has been used after coming into contact only once with a human body. In most cases, such as blood sample collection, it is necessary to remove the needle or other device from the medical tool and it is during this process that many occurrences of injury occur. Such injuries are referred to as needle stick injuries and it is to the prevention of needle stick injuries that this present invention is directed.

A further problem is that the procedure for the disposal of the sharps or needles at present whether or not they have been removed from a syringe is to drop them into a storage container which may then be destroyed by burning or the like. It is found, however, that needles may tend to puncture and project out of the sides of a container into which they have been placed and cause problems for disposal personnel as well. Hence, this invention is directed to preventing needles from being able to create further injury once they have been dropped into a disposal container.

It is one object of this invention, therefore, to alleviate the necessity to handle a needle or the boss of a needle during disposal process and to prevent that needle from being able to cause any further injury once removed.

Jagger et al. U.S. Pat. No. 4,592,744, describes a self re-sheathing safety case for a needle but this requires a special construction of syringe and even with its relative complexity is not entirely fool-proof.

U.S. Pat. No. 4,576,281 describes a needle disposal system in which needles are safely removed and dropped into a container but the point of the needle is still exposed in the container and as indicated can and often does penetrate the walls of the container and cause problems to disposal personnel.

It is to overcoming these various problems that this present invention is directed.

In one form therefore, the invention is said to reside in a sheath for the disposal of medical sharps, the sheath comprising a tubular portion closed at one end and being open at the other, the open end of the sheath having a radially outwardly extending flange, the flange including means to guide the tip of a medical sharp into the tube and the inner surface of the tube in the region of the flange including means to grippingly engage a boss portion of the medical sharp.

Therefore, this sheath is long enough to completely encase the needle or sharp and then holds it rigid so that the needle or sharp cannot project out of the sides of the sheath or the bottom of the sheath. Once the boss of the medical sharp is received and held in the gripping portion of the tube the syringe or other device can be rotated to release the sharp form the medical tool and then one or either parts can be disposed of. Alternatively, the medical tool and the attached sharp may be disposed of as a single unit with complete safety.

Preferably, the outer surface of the tube adjacent to the flange includes ribs to assist with grasping of the sheath for the removal process.

The means to grippingly engage the boss of a medical sharp may include a plurality of longitudinal ridges extending radially inward from the inner surface of the tube to enable gripping of the boss by the ridges.

Alternatively, the means to grippingly engage the boss of the medical sharp may include an inside portion of the tube being substantially cylindrical and having a diameter to engage with an interference fit the boss of the medical sharp.

The means to guide the tip of the medical sharp into the tube may comprise a bevelled surface between the flange and the inner surface of the tube.

In another form, the invention may reside in a medical sharp disposal rack comprising a tray having an upper substantially planar horizontal surface with a plurality of apertures thereon, the apertures receiving and supporting a plurality of sheaths as defined above with their open ends upward.

By this means the sheath may be supported during the removal stage so that the user's second hand may be kept completely away from the tip of the medical sharp thereby completely eliminating any danger. Once the boss of the medical sharp has been firmly engaged in the gripping portion of the tube, then the sheath, while still connected to the medical tool, may be removed from the tray and either disposed of as discussed above as a complete unit, or the sheath with the sharp engaged therein can be removed from the medical tool and disposed of separately.

Alternatively, the invention may be said to reside in a medical sharp disposal tray having an upper substantially planar and horizontal surface with a plurality of tubes extending from apertures in the surface and having closed lower ends, each tube having a bevelled portion between the planar surface and the inner surface of the tube to assist with guiding the tip of a medical sharp into the tube and having means to grippingly engage the boss at the base of a medical sharp when inserted into the tube.

By this form of the invention the medical sharps may be received in the tubes in the disposal tray and then when all of the tubes in the tray are full the entire lot may be disposed of.

It will be realized that where medical sharps have different arrangements of bosses or gripping means at the base of their pointed section then other gripping means are within the scope of this invention to enable the pointed section to be clearly protected as described above.

It will be noted that with the various forms of the invention as discussed above it is not necessary for a user to remove the needle section manually from the medical tool before it is inserted into the sheath. Therefore, there is much less chance of injury from the medical sharp.

It may not be necessary for the user to remove the needle section from the medical tool prior to disposal and in this situation a firm downward movement of the sheath onto a hard surface, once it is installed onto the medical sharp, will more tightly affix the sheath to the needle section of the medical tool and the needle section to the medical tool itself so that the medical tool and sharp and sheath can be disposed of as a single unit. This again provides considerable safety because the needle cannot enter the user.

If desired, there may be further provided within each tube of either the sheath or the fixed construction as discussed above, a foam or other compound to assist with holding a needle where perhaps such needles do not have a boss which will be easily engaged into the sheath.

In general, therefore, this invention provides a safe method for the removal of medical sharps from a medical tool and their disposal and hence in a further embodiment the invention is said to reside in a method of safe removal of medical sharps from medical tools and the disposal of medical sharps substantially as earlier discussed. It will be particularly noted that the method requires only a one handed operation and hence as one hand is holding the medical tool the other hand can be placed well away so that there is no danger of a needle piercing the skin of a user and perhaps transmitting a disease such as AIDS.

This generally describes the invention but to more clearly assist with understanding the invention reference will now be made to the accompanying drawings which show preferred embodiments of the invention and show how the invention is used.

DESCRIPTION OF THE PREFERRED EMBODIMENTS

Figure 1:
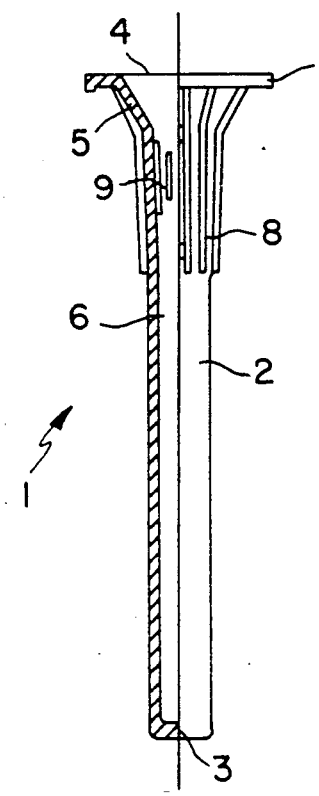
FIG. 1 shows in part cross-section of a sheath for the removal and disposal of medical sharps.

Now looking more closely at the drawings and in particular FIG. it will be seen that the sheath generally shown as 1 comprises a tubular portion 2 having a closed end 3 and an open end 4. The open end has a bevelled inner surface 5 to assist with guiding the tip of a medical sharp into the hollow part 6 of the tube 2. A flange 7 extends radially outwardly from the open end 4 of the sheath 1 and the size of the flange is such that if the sheath is held by the fingers then the fingers will be substantially guarded by the flange. On the outside of the sheath 1 are a number of ridges 8 underneath the flange 7 so that the outside of the sheath may be grasped while the needle is being removed from a syringe or other article of medical equipment once the boss has been engaged in the tube. To assist with engaging the boss into the tube, the inner surface of the tube 2 immediately adjacent the open end includes longitudinal ridges 9 which engage the boss of a medical sharp to assist with removal.

Figure 2:
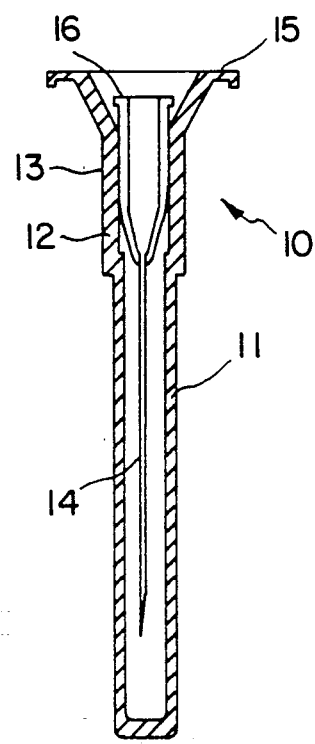
FIG. 2 shows a cross-sectional view of an alternative sheath for the removal of medical sharps with a hypodermic syringe needle in the sheath.

An alternative embodiment of medical sharp removal is shown in FIG. 2 with a hypodermic syringe needle engaged therein. In this embodiment the gripping region 10 of the tube 11 includes a substantially cylindrical inner surface 12 to engage with an interference fit around the boss 13 of a medical sharp. It will be seen that the needle 14 of the medical sharp is well protected in the sheath and cannot move sideways and pierce the walls of the tubular portion of the sheath.

It will also be noted that the top 16 of the boss is recessed well below the flange area 15 and hence the medical sharp cannot easily be removed for illegal further use.

Figure 3:
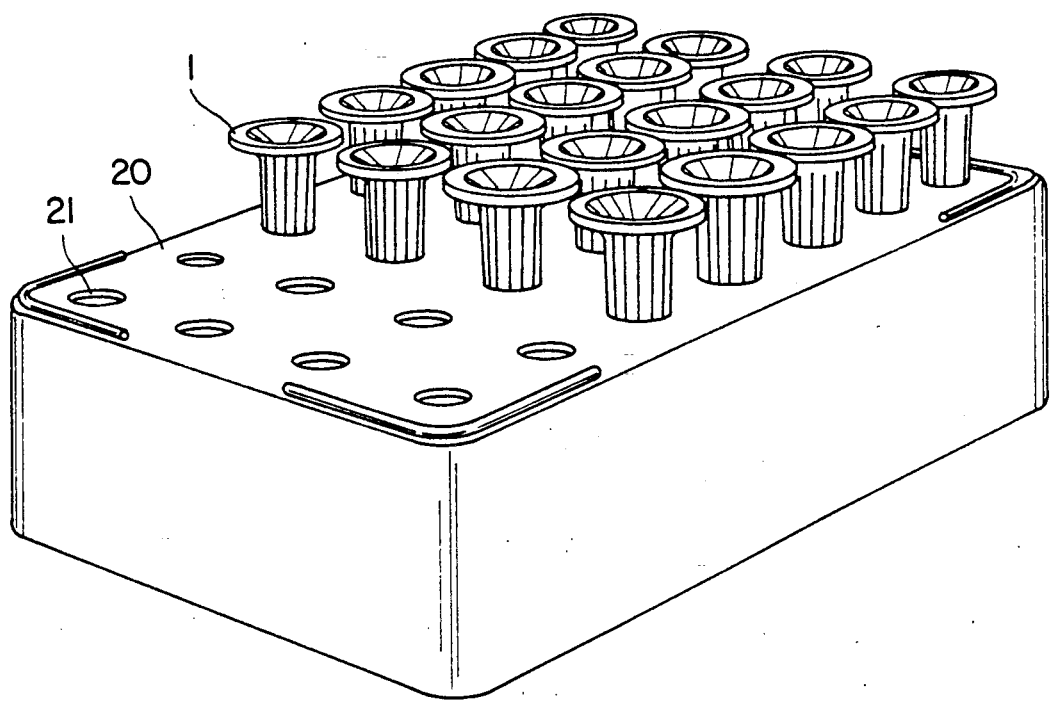
FIG. 3 shows a disposal tray with a number of sheaths supported therein.

FIG. 3 shows a number of sheaths 1 engaged in a tray 20. The tray includes a number of apertures 21 into which the sheaths 1 are received. The sheaths are supported in the tray but can easily be removed as they are loosely held.

Figure 4:
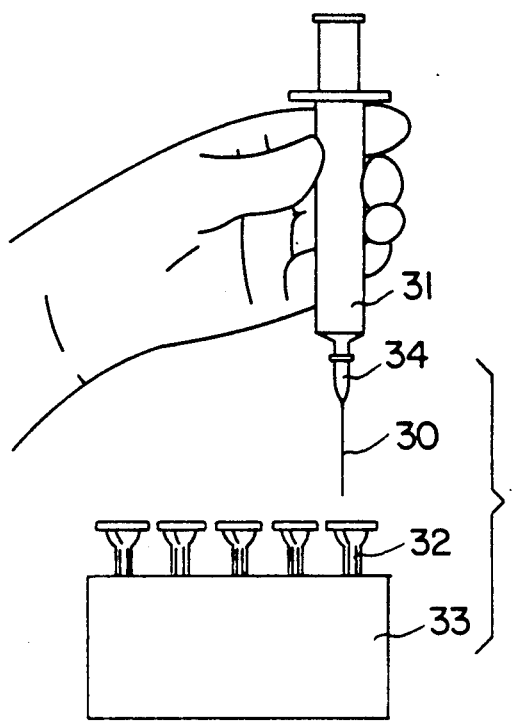
FIGS. 4 to 8 show the various stages in the process of removal of a medical sharp from a hypodermic syringe.

Now looking at FIGS. 4 to 8 which show the various stages in the removal of a needle, it will be seen in FIG. 4 that a syringe is being held in one hand with the point 30 of the syringe 31 pointed down into one of the sheaths 32 supported in the tray 33. It will be noted that only one hand is necessary to hold the syringe and the other hand is completely away from the tray 33.

Figure 5:
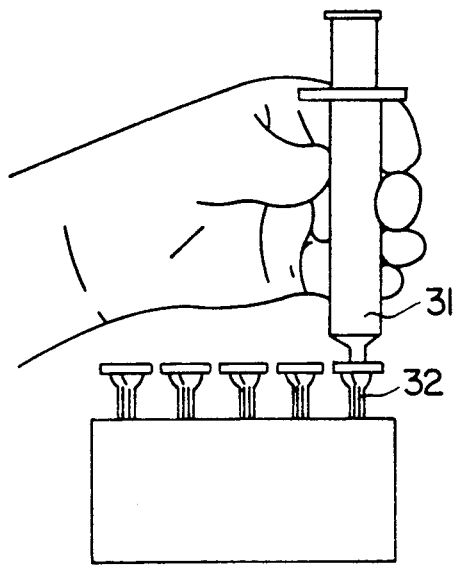
Figure 6:
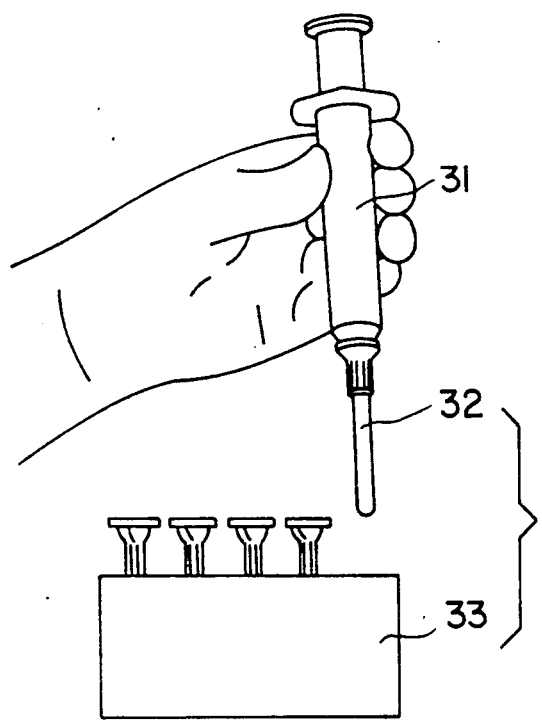
Figure 7:
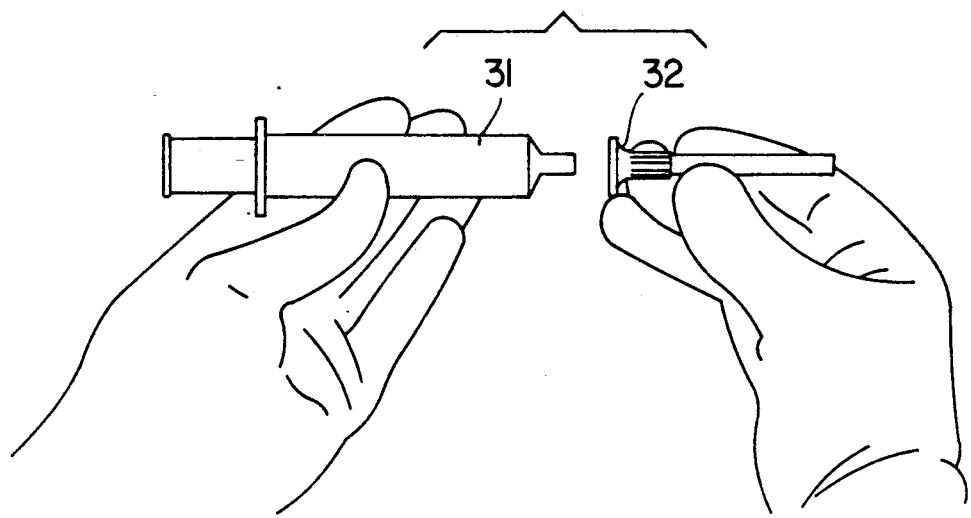

The needle 30 is pushed into the tube of the sheath 32 until the boss 34 as shown in FIG. 4 is completely pushed into the tube as can be seen in FIG. 5. As can be seen in FIG. 6 the sheath 32 is then engaged onto the syringe 31 and the sheath is removed from the tray 33. Then, as shown in FIG. 7, both hands can be used to remove the sheath 32 from the tool 31 leaving the needle fully protected by the sheath.

Figure 8:
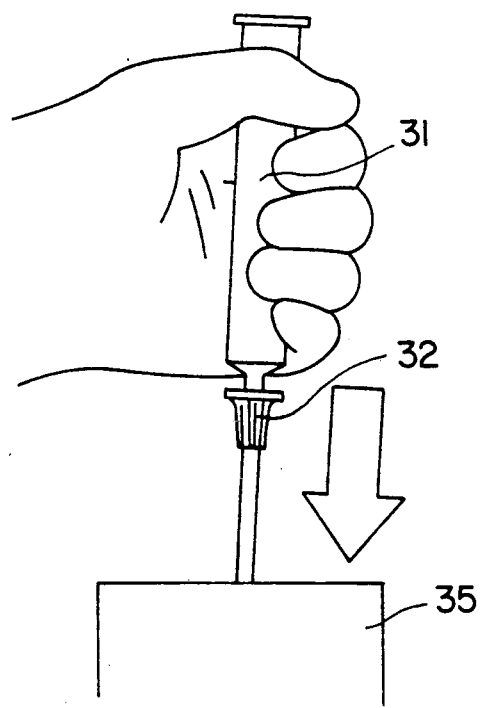

Alternatively, as shown in FIG. 8, from the stage shown in FIG. 6 the medical tool 31 with the sheath 32 engaged can be struck onto a hard surface 35, thereby firmly engaging the boss of the needle into the sheath and the syringe firmly into the boss so that the two portions can be disposed of together.

Figure 9:
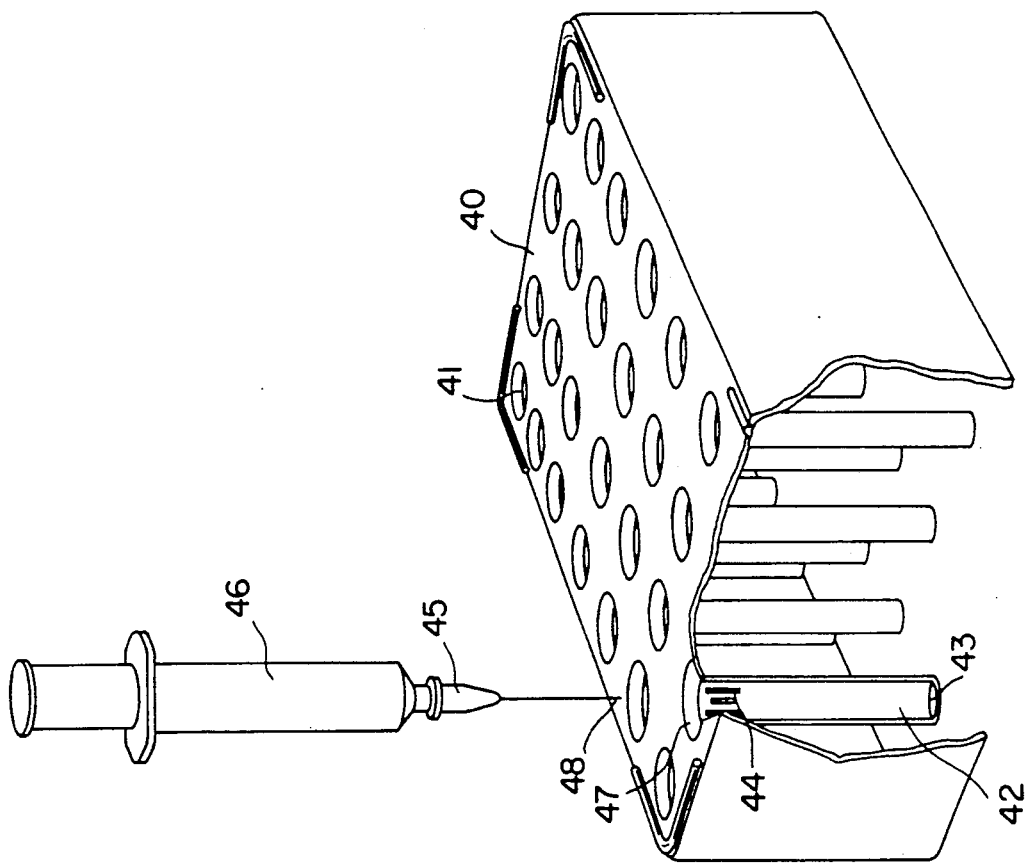
FIG. 9 shows an alternative embodiment of a medical sharp disposal tray.

FIG. 9 shows an alternative embodiment where a tray 40 includes a number of apertures 41. Each aperture includes a tubular portion 42 closed at its lower end 43 and including gripping ribs 44 to engage the boss 45 of a syringe 46. There is a bevelled portion 47 between the planar upper surface of the tray 40 and the tube 42 to assist with guiding the point 48 of a needle into the tube. Once the boss 45 has been firmly engaged in the tube 42, then the syringe 46 may be twisted to remove the needle therefrom and to leave the needle firmly engaged in the tray 40. Once all of the apertures in the tray have been filled the tray as a whole may then be disposed of.

The materials of construction of the sheath and tray or molded sheath and tray combination may be any plastic material such as polyethylene or polypropylene. Alternatively, the tray may be made from cardboard, stainless steel or other suitable materials. Stainless steel and plastic offer the advantages of durability and easy clean-up, and stainless steel allows for sterilization of the materials. For plastic materials, the preferred method of construction is by injection-molding but other methods may be used.

Figure 10:
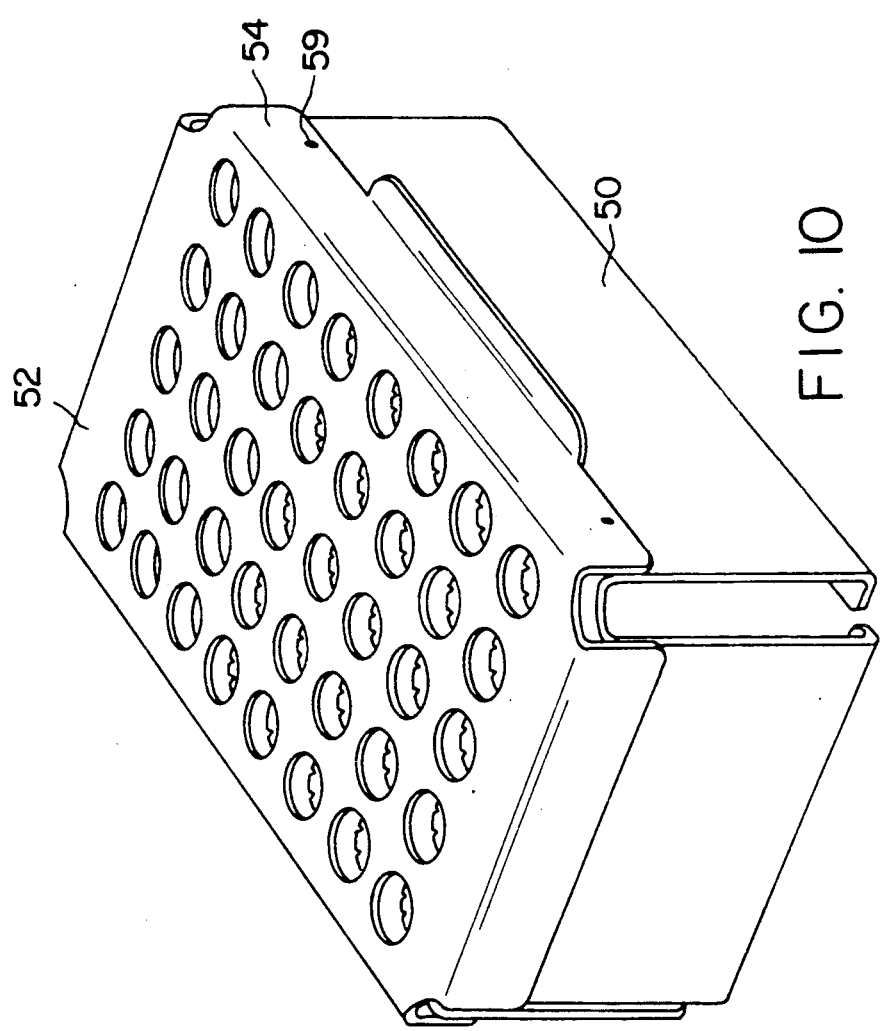
FIG. 10 shows an alternative embodiment of a medical sharp disposal tray system which includes a cover.
Figure 11:
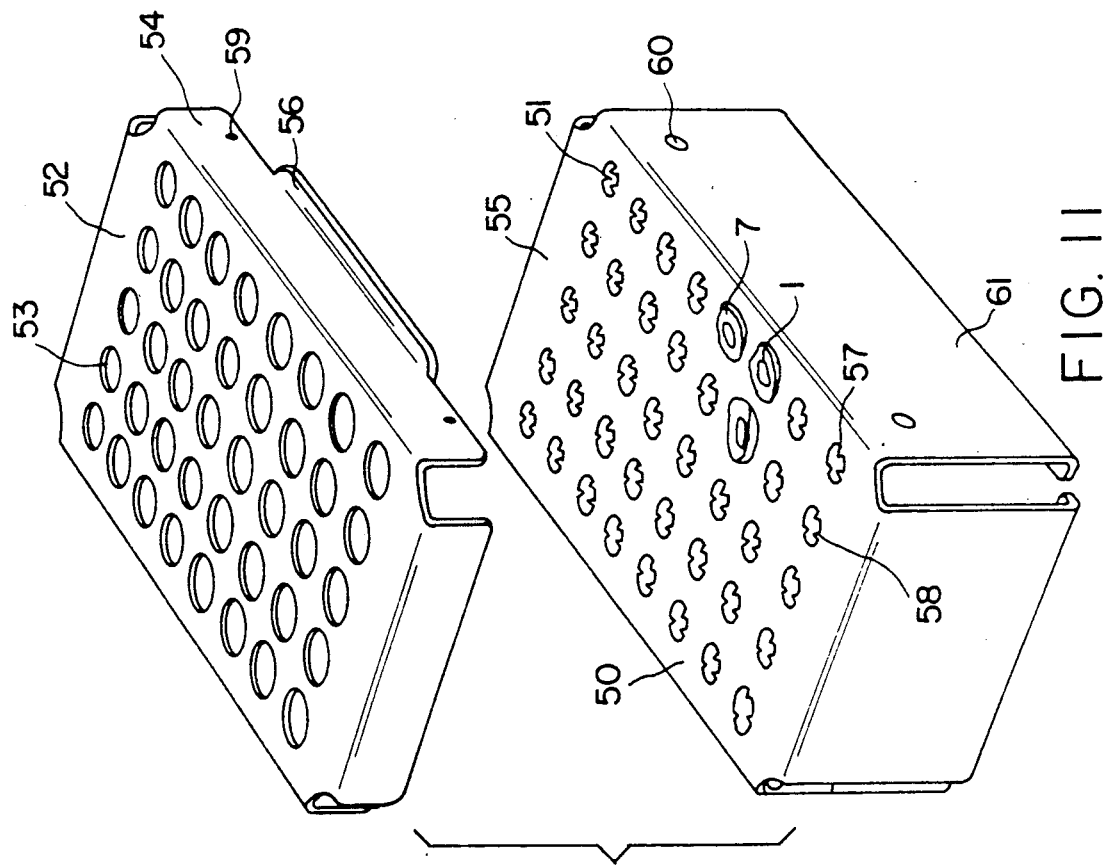
FIG. 11 is an exploded view of the medical sharp disposal tray system of FIG. 10.
Figure 12:
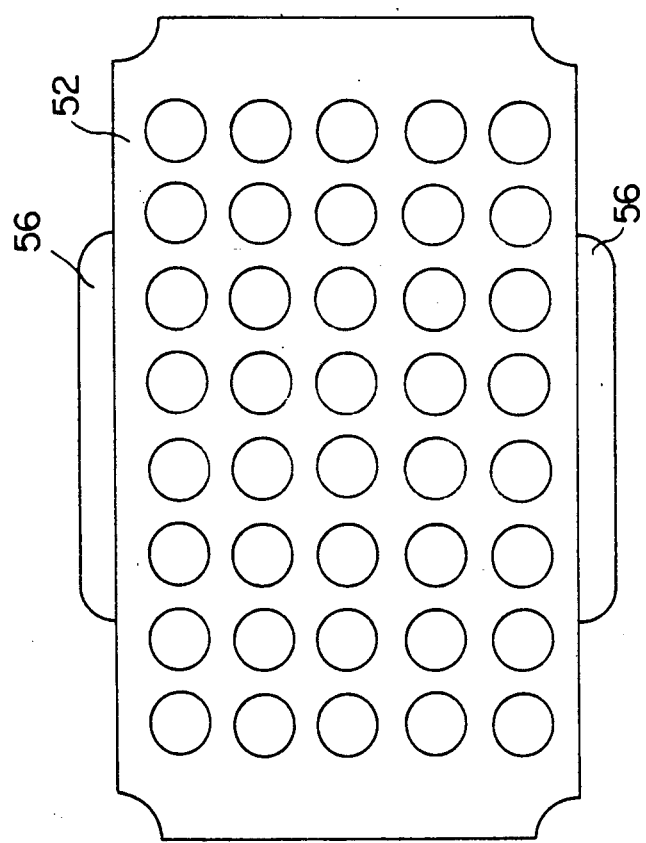
FIG. 12 is a top view of the cover of FIGS. 10 and 11.

FIGS. 10, 11 and 12 show an alternative embodiment wherein a tray 50 includes a plurality of apertures 51. Each aperture 51 receives a sheath 1. The sheath 1 is provided with a flange 7, and the sheath 1 is supported by an aperture 51 such that the flange 7 rests on a planar surface 55 of the tray 50. A cover 52 is provided with a plurality of apertures 53, with the arrangement of apertures 53 of the cover 52 corresponding to the arrangement of apertures 51 in the tray 50, although it is not necessary that the size of the apertures 53 correspond to the size of the apertures 51. The cover 52 is placed over the tray 50 containing sheaths 1 in the apertures 51.

If desired, the cover can be provided with alignment means, such as the edge 54 which extends perpendicularly from the top planar surface 53, so that the cover will nest securely over the tray 50. Additionally, the cover can include gripping means, such as the protrusion 56 extending perpendicularly and outwardly from the edge 54. The gripping means assists a user in removing the cover by gripping this gripping means.

The cover 52 also includes detents 59 on the edges 54 which engage corresponding detents 60 on the sides 61 of the tray 50. The interengagement of the detents 59 and 60 holds the cover 52 firmly onto the tray 50 with the flanges 7 of the sheaths between the tray surface and the cover so that even accidental dropping of the tray will not dislodge the cover and thereby cause the sheaths to spill out. For example, each detent 59 forms a protrusion on the inner surface of edge 54. Each detent 60 forms an indentation in the outer surface of sides 61, such that each detent 60 corresponds to a detent 59. Alternatively, the detent 60 could form a protrusion on an outer surface of sides 61, while the detent 59 would form an indentation in the inner surface of edge 54.

The apertures 51 may be substantially circular to correspond to the diameter of an upper portion of the sheath. Additionally, as illustrated in FIG. 11, in a preferred embodiment the apertures 51 are substantially circular and may include sheath engagement means 57 so that they may securely engage a sheath within the aperture. As shown in FIG. 11, the engagement means for each aperture 51 comprises a plurality of teeth 58 extending radially inward from the circumference of a circular aperture. The teeth 58 engage the vertical ridges 8 (see FIG. 1) underneath the flange 7 of the sheath 1, thereby preventing the sheath from turning in the aperture 51 while removal of a needle from a syringe is carried out.

In operation of this disposal system, a user places a number of sheaths into the apertures 51 of the tray 50. Subsequently, the cover is placed on the tray, and the detents 59 and 60 are interengaged to firmly hold down the cover onto the tray, as shown in FIG. 10. A user can now insert medical sharps into the sheaths, with the cover providing an additional securing of the sheaths during insertion of the sharp into the sheath, since the cover rests on the flange. Thus, only a one-handed operation is necessary for the insertion of a needle into a sheath. The cover further serves to help prevent sheaths from falling from the tray.

In removing the medical sharp once the needle portion is engaged in the sheath, a user can proceed to remove the instrument while the needle stays engaged in the sheath.

In a preferred method of using the apparatus, the tray, with the cover removed, is filled with a desired number of sheaths. Subsequently, the cover is placed on the tray which contains sheaths, and a user can now safely disengage the boss portion of a medical sharp in the sheaths. When the user is ready to empty the tray of sheaths with needles engaged therein, the cover is removed, and the sheaths can be disposed of by simply inverting the tray and dumping the sheaths out of the tray and into a disposal container.

The cover and tray in this embodiment may be constructed of any suitable material, as in the other embodiments, with stainless steel or plastic being preferred. Further, it is apparent that the tray may be constructed of any desired size, with any desired number of apertures. For example, if the tray assembly is to be transported between different locations by a user, such as from room to room in a hospital or a medical lab, the apparatus would be small and light enough to be conveniently carried by a user.

What is claimed is:

1. An apparatus for supporting a plurality of sheaths for receiving and holding medical sharps, each sheath comprising a tubular portion closed at a lower end and open at an upper end and further having a flange around said upper end, said apparatus comprising:
   holding means comprising a planar surface with a plurality of apertures therein, each aperture having a configuration to receive and support one of said sheaths toward an upper end of the sheath; and
   cover means for covering the planar surface of the holding means, said cover means comprising a planar surface with a plurality of apertures therein, each said aperture having a configuration to prevent passage of said flange therethrough, said plurality of apertures in the cover means arranged to substantially correspond to an arrangement of the apertures in the holding means.

2. The apparatus of claim 1, wherein said planar surface of the holding means is substantially horizontal and the sheaths are held in an upright position in said holding means.

3. The apparatus of claim 1, wherein the cover means further includes alignment means for aligning the cover on the holding means.

4. The apparatus of claim 3, wherein the alignment means comprises an edge extending perpendicularly downward from the planar surface of the cover means.

5. The apparatus of claim 4, wherein the planar surface of the cover means comprises four sides, and an edge extends perpendicularly downward from each side of the planar surface of the cover means.

6. The apparatus of claim 4, wherein the cover means further includes gripping means to assist a user in removing the cover means from the holding means.

7. The apparatus of claim 6, wherein the alignment means comprises two of said edges extending from two opposed sides of the planar surface of the cover means, and the gripping means comprises a protrusion extending perpendicularly and outwardly from each of said two edges.

8. The apparatus of claim 4, further including interengagement means for securing the cover means to the holding means.

9. An apparatus for supporting a plurality of sheaths for receiving and holding medical sharps, each sheath comprising a tubular portion closed at a lower end and open at an upper end, said apparatus comprising:
   holding means comprising a planar surface with a plurality of apertures therein, each aperture for receiving and supporting one of said sheaths toward an upper end of the sheath;

cover means for covering the planar surface of the holding means, said cover means comprising a planar surface with a plurality of apertures therein, said plurality of apertures in the cover means arranged to substantially correspond to an arrangement of the apertures in the holding means, and further comprising alignment means including an edge extending perpendicularly downward from the planar surface of the cover means, and interengagement means for securing the cover means to the holding means, wherein the holding means includes side portions extending perpendicularly downward from said planar surface, said interengagement means comprising a protrusion of an inner surface of said edge of the cover means and a corresponding indentation in an outer surface of the side portions of the holding means for interengaging said protrusion.

10. The apparatus of claim 9, wherein two edges extend from two opposed sides of the planar surface of the cover means, each of said two edges including two protrusions on their inner surfaces, and the side portions of the holding means include corresponding indentations for each of said protrusions.

11. The apparatus of claim 1, wherein the apertures in the holding means include sheath engagement means.

12. The apparatus of claim 8, wherein each aperture in the holding means is substantially circular, and the sheath engagement means comprises a plurality of teeth extending radially inward from the circumference of the aperture for engaging a sheath.

13. The apparatus of claim 1, wherein the holding means and the cover are each constructed of stainless steel.

14. The apparatus of claim 1, wherein the holding means and the cover are each constructed of plastic.

15. An apparatus for supporting a plurality of sheaths for receiving and holding medical sharps, said apparatus comprising:

a plurality of said sheaths, each sheath comprising a tubular portion closed at a lower end and open at an upper end, holding means comprising a planar surface with a plurality of apertures therein, each aperture for receiving and supporting one of said sheaths toward an upper end of the sheath; and cover means for covering the planar surface of the holding means, said cover means comprising a planar surface with a plurality of apertures therein, said plurality of apertures in the cover means arranged to substantially correspond to an arrangement of the apertures in the holding means.

16. The apparatus of claim 15, wherein the open upper end of said sheaths includes means to assist in guiding a tip of a medical sharp into the sheath.

17. The apparatus of claim 16, wherein said means to assist in guiding the tip of the medical sharp into the sheath comprises a bevelled surface at the upper end of the sheath.

18. The apparatus of claim 15, wherein an upper inner surface of said sheaths includes means to grippingly engage a boss portion of a medical sharp.

19. The apparatus of claim 18, wherein said means to grippingly engage includes a plurality of ridges extending radially inward from the inner surface of the tubular portion.

20. The apparatus of claim 18, wherein said means to grippingly engage includes an inside portion of the tubular portion being substantially cylindrical and having a diameter to engage with an interference fit the boss of a medical sharp.

21. The apparatus of claim 15, wherein each sheath includes a flange around the upper end of the tubular portion for supporting the sheath in the aperture of the holding means such that the flange rests on a portion of the planar surface of the holding means adjacent to said aperture.

* * * * *